United States Patent [19]

Meryman

[11] Patent Number: 5,770,069

[45] Date of Patent: Jun. 23, 1998

[54] COLLAPSIBLE CONTAINER FOR HOLDING A FLUID DURING A CENTRIFUGATION OPERATION

[75] Inventor: Harold T. Meryman, Ashton, Md.

[73] Assignee: Organ, Inc., Chicago, Ill.

[21] Appl. No.: 803,880

[22] Filed: Feb. 21, 1997

Related U.S. Application Data

[62] Division of Ser. No. 483,265, Jun. 7, 1995, Pat. No. 5,656,154.

[51] Int. Cl.[6] ................................................. B01D 21/26
[52] U.S. Cl. ................... 210/255; 210/360.1; 210/361; 210/512.3; 210/782; 422/72; 422/918; 494/21; 494/32; 604/410
[58] Field of Search .............................. 684/410; 494/32, 494/37, 16, 21; 210/782, 787, 772, 789, 252, 261, 198.1, 255, 206, 360.1, 380.1, 513, 94, 97, 515, 143, 512.1, 512.3, 361; 422/9, 8, 72

[56] References Cited

U.S. PATENT DOCUMENTS

| | | |
|---|---|---|
| 463,794 | 11/1891 | De Laval . |
| 559,065 | 4/1896 | Salenius . |
| 1,815,409 | 7/1931 | Knuttel . |
| 2,779,537 | 1/1957 | Madany . |
| 3,064,647 | 11/1962 | Earl . |
| 3,513,976 | 5/1970 | James . |
| 3,545,671 | 12/1970 | Ross . |
| 4,040,959 | 8/1977 | Berman et al. . |
| 4,146,172 | 3/1979 | Cullis et al. . |
| 4,187,979 | 2/1980 | Cullis et al. . |
| 4,213,561 | 7/1980 | Bayham . |
| 4,413,771 | 11/1983 | Rohde et al. . |
| 4,482,342 | 11/1984 | Lueptow et al. . |
| 4,617,009 | 10/1986 | Ohlin et al. . |
| 4,804,363 | 2/1989 | Valeri . |
| 4,892,668 | 1/1990 | Harmony et al. . |
| 5,045,185 | 9/1991 | Ohnaka et al. . |
| 5,092,996 | 3/1992 | Spielberg . |
| 5,102,407 | 4/1992 | Carmen et al. . |
| 5,141,645 | 8/1992 | Shiraki et al. . |

*Primary Examiner*—David A. Reifsnyder
*Attorney, Agent, or Firm*—Oliff & Berridge, PLC

[57] ABSTRACT

A method and apparatus for sterile separation of a fluid into components, for washing of a material, and for preparing a washed, separated material for refrigerated storage includes rotating the fluid or material in a multi-chambered container to accomplish a centrifuging operation. An apparatus embodying the invention may include an elongated, collapsible container having plural chambers connected in series by necks. The multi-chambered container may be formed of a single flexible bag having plural chambers. Alternately, the container may comprise plural flexible bags, each of which comprises one or more of the chambers of the container. A chamber of the container may be separated into plural sections by partition walls, each of the sections of the chamber being connected to an adjacent chamber by a separate branch of a neck between the chambers. An apparatus for rotating the container may include a holder for supporting the container during rotation, and a centrifuge for rotating the container and the holder. In addition, the apparatus for rotating the container may include clamping devices for closing off the necks and detectors mounted adjacent the necks for detecting movement of material through the necks.

13 Claims, 7 Drawing Sheets

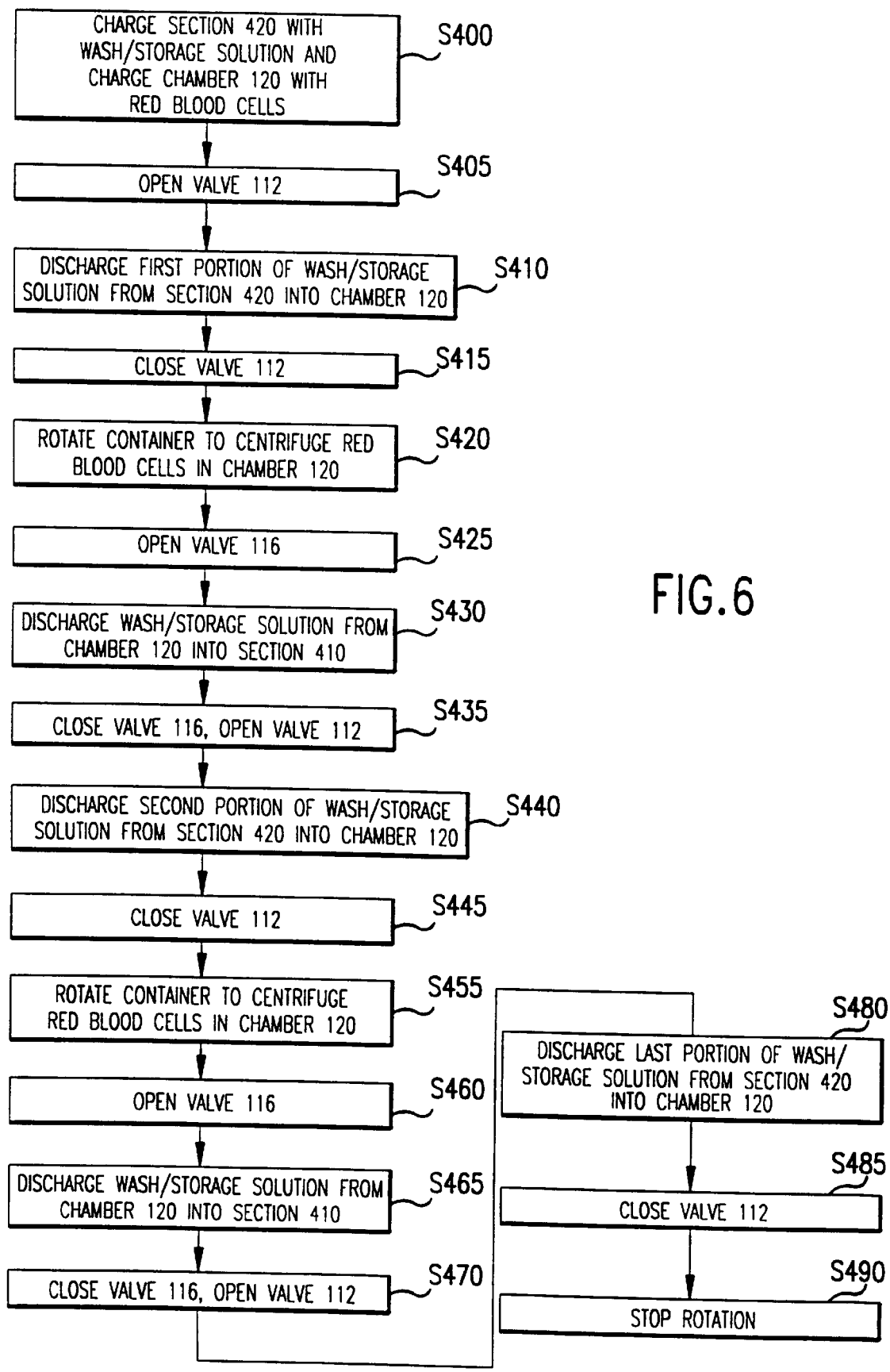

COLLAPSIBLE CONTAINER FOR HOLDING A FLUID DURING A CENTRIFUGATION OPERATION

This is a Divisional of application Ser. No. 08/483,265 filed Jun. 7, 1995, now U.S. Pat. No. 5,654,154.

BACKGROUND OF THE INVENTION

The invention is related to methods and apparatus for separating a fluid into components, and for washing or deglycerolizing a material. The invention is particularly useful for separating whole blood into components and for washing or deglycerolizing separated red blood cells.

Most existing devices for separating a fluid into components utilize a centrifuge to separate heavier components from lighter ones. For instance, U.S. Pat. No. 5,141,645 to Shiraki et al., the disclosure of which is hereby incorporated by reference, describes a blood separation method utilizing a centrifuge. In this system, whole blood is collected in a flexible bag, and the bag is then subjected to a centrifuging operation that causes the heavier blood components (such as red blood cells) to settle at the bottom of the bag. After centrifuging, the lighter blood components, such as plasma and platelets, are drawn off the top of the bag and conducted to a separate container, and the heavier components are left behind in the bag.

Existing systems for separating components of whole blood require multiple separate centrifuging steps. Typically, whole blood in a first container is inserted in a centrifuge and separated into red blood cells and, platelet rich plasma in a first centrifuging operation. The centrifuge is then stopped, the first container is removed from the centrifuge, and the platelet rich plasma is separated from the red blood cells and placed in a second container. The second container, and the platelet rich plasma, are then placed in the centrifuge and, subjected to a second centrifuging operation that separates the platelets from platelet poor plasma. The centrifuge is again stopped, the second container is removed from the centrifuge, and the platelet poor plasma is separated from the platelets and placed in a third container. These existing methods of separating whole blood are labor intensive and time consuming. As a result, the separation procedures are relatively expensive to perform.

It is also desirable to wash separated red blood cells to fully remove plasma and platelets prior to storage of the red blood cells. Washed red blood cells can be stored at refrigeration temperatures for much longer periods of time than un-washed red blood cells. Unfortunately, the cost of performing a washing procedure using conventional apparatus is relatively high. As a result, washing of red blood cells is not typically performed.

In addition, in a similar procedure, thawed red blood cells that have been stored in a cryoprotective glycerol solution must be washed to remove the glycerol prior to transfusing the red blood cells into a subject. The cost of performing the deglycerolization procedure is an obstacle to use of thawed red blood cells.

In one type of red blood cell washing/deglycerolizing device, a wash solution is introduced into a container holding the red blood cells, and the solution is mixed with the red blood cells to accomplish washing. The container is then subjected to a centrifuging operation to cause the red blood cells to collect on the bottom of the container. The used wash/deglycerolization solution is drawn off the top of the container, leaving washed/deglycerolized red blood cells on the bottom of the container.

Other washing/deglycerolizing devices user a cylindrical chamber that is rotated to force washed red blood cells against the exterior walls of the cylindrical chamber. The wash/deglycerolization solution can then be drained from the cylinder along the axis of rotation. Such red blood cell washing devices incorporate rotating seals that permit introduction and removal of the wash solution. As a result, such systems are relatively complex and expensive, and can be costly to operate because the rotating seals must be replaced after each use.

Another type of red blood cell washing device under investigation utilizes cross-flow filtration. These devices, however, are even more expensive to operate than the centrifuging apparatus described above.

SUMMARY OF THE INVENTION

The invention relates to methods and apparatus for separating a fluid into components and for washing or deglycerolizing a material. An apparatus embodying the invention, as shown in FIGS. 1, 3, 5A–5D and 7 includes an elongated, collapsible container having at least two chambers connected in series fashion by tubular necks. The walls of the chambers are flexible to permit the chambers to be at least partially collapsed. The apparatus also includes automated or manual closure devices for closing off the necks between the chambers to keep contents of the chambers separate. The apparatus may also include sensors for sensing the passage of material through the necks.

Methods embodying the present invention utilize the apparatus described above to separate fluids into components. A fluid is placed in one of the chambers and the entire container is rotated around its longitudinal central axis to accomplish a centrifuging operation. The centrifuging causes the heavier components of the fluid to collect around the periphery of the chamber, while the lighter components collect along the longitudinal central axis of the chamber. After the fluid has been separated by centrifuging, a closure device on a neck between adjacent chambers is opened, and pressure is applied to an exterior wall of the chamber holding the fluid to partially collapse the chamber. The partial collapse of the chamber discharges the lighter components of the fluid collected along the longitudinal central axis of the chamber into an adjacent chamber through the neck between the chambers. When the heavier components begin to exit the chamber through the neck, the closure device is closed to keep the separated components in different chambers.

Other methods embodying the invention accomplish washing or deglycerolization of a material using the apparatus described above. At the beginning of the method the material is in one chamber of the container, and a washing solution is in an adjacent chamber. The closure device on the neck between the chambers is opened, and pressure is applied to an exterior wall of the washing solution chamber to cause the washing solution to be discharged into the chamber holding the material. The washing solution may be thoroughly mixed with the material by intermittent rotation of the container, then the container is continuously rotated around its longitudinal central axis to perform a centrifuging operation on the mixture. The centrifuging causes the material to collect around the periphery of the chamber, while the washing solution collects along the longitudinal central axis of the chamber. The closure device is then opened, and pressure is applied to an exterior wall of the mixing chamber to discharge the washing solution from the mixing chamber, back into the chamber in which it was originally held. When the material begins to enter the neck between the chambers, the closure device is closed to keep the washed material separate from the used washing solution.

Detailed descriptions of methods and apparatus embodying the present invention are provided in the description which follows.

BRIEF DESCRIPTION OF THE DRAWINGS

Embodiments of the present invention will be described with reference to the following drawing figures, wherein like features are identified with like reference numbers, and wherein:

FIG. 6 is a flow chart of another method embodying the invention that utilizes the apparatus of FIG. 5;

DETAILED DESCRIPTION OF PREFERRED EMBODIMENTS

In the description that follows, the invention may be described with reference to separation of whole blood and washing or deglycerolizing separated red blood cells. However, the invention is equally applicable to separation of any fluid that can be separated into components by centrifuging, and washing or deglycerolizing of any material. Thus, any references to whole blood, component parts of whole blood, and washing or deglycerolizing red blood cells is not intended to be limiting, and these terms should be understood to encompass any fluid capable of separation by centrifuging, materials to be washed or deglycerolized, and washing or deglycerolizing of a material, respectively.

Figure 1:
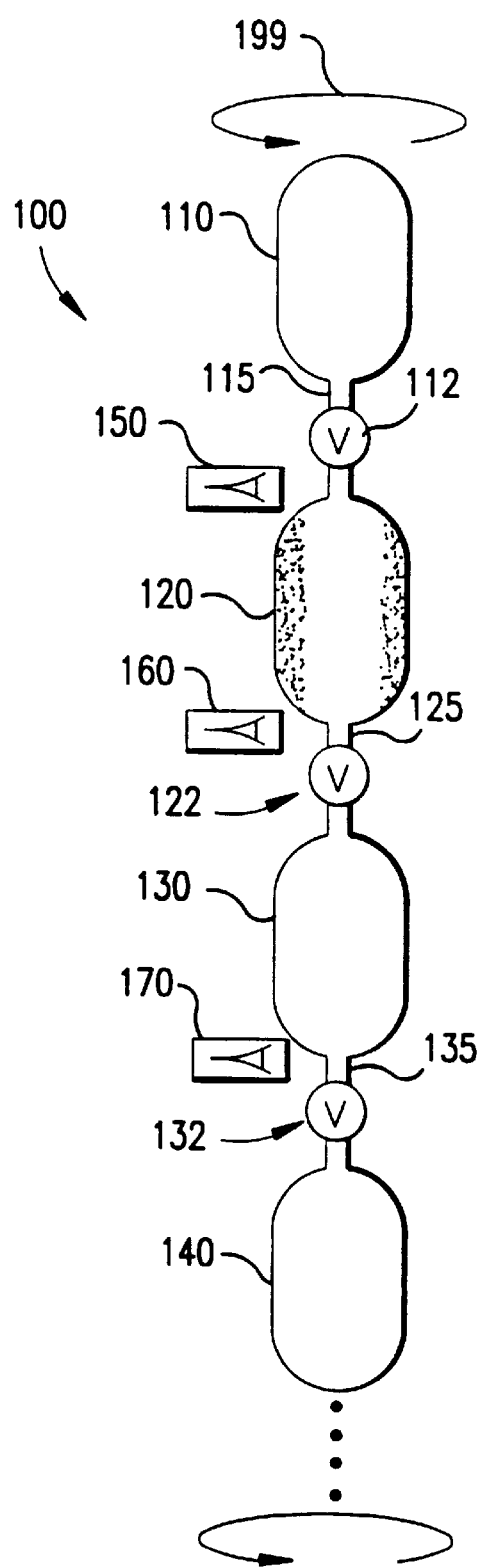
FIG. 1 is a diagram of an apparatus embodying the invention.

FIG. 1 shows an apparatus embodying the invention that includes a collapsible, elongated container 100 having four chambers 110, 120, 130, 140 joined in series by three necks 115, 125, 135. A closure device 112 may be mounted adjacent a neck 115 between chambers 110 and 120. Likewise, closure devices 122 and 132 may be mounted adjacent necks 125 and 135, respectively. Sensors 150, 160 and 170 may also be positioned adjacent the necks 115, 125 and 135 to sense when a material enters a neck leading into an adjacent chamber.

The container 100, may be mounted on a holder for supporting the container during rotation. The holder can then be mounted on a rotation apparatus that rotates the holder and the container around a longitudinal central axis of the container, as indicated by arrow 199. Alternately, the container may be directly mounted on the rotation device, and the container may be rotated without supporting the walls of the container. A description of such a holder and rotation device are provided below.

The rotation of the container 100 performs a centrifuging operation on the contents of the chambers. Heavier components in a chamber collect around the periphery of the chamber, while lighter components collect along the longitudinal central axis of the chamber. Ideally, during rotation of the container 100, the longitudinal central axes of the chambers and the necks are coincident with the longitudinal central axis of the container 100.

The contents of a first chamber may be moved into a second, adjacent chamber by opening a closure device for the neck between the chambers and applying pressure to an exterior wall of the first chamber. Because the walls of the container are flexible, the applied pressure will cause the first chamber to partially collapse. The partial collapse of the first chamber will discharge part of the contents of the first chamber into the second chamber through the neck. If this operation is accomplished while the container is being rotated about its longitudinal central axis, only the contents collected along the longitudinal central axis of the first chamber will be discharged through the neck.

The application of pressure to an exterior wall of a chamber may be accomplished by providing weighted arms that are attached to pressure plates which bear against the exterior of the chambers. As the container is rotated, the weighted arms are subjected to the same centrifugal forces as the contents of the chambers. An appropriately designed lever system will cause the weighted arms to apply pressure to the pressure plates during rotation, and the pressure plates will, in turn, compress the container.

Alternately, the application of pressure to the exterior of a chamber could be accomplished by surrounding the chamber with an inflatable collar, then partially inflating the collar with compressed air. In yet another embodiment, compressed air jets could be directed against the exterior of a chamber to apply a force to the chamber. The air jets could be sized and directed to apply pressure to selected portions of the exterior of the chamber.

The pressure applying means should be designed to apply pressure to the exterior walls of the container so that only the contents along the longitudinal central axis of a chamber are discharged through a neck. Thus, the exact configuration of the pressure applying means will depend on the shape of the container, and the force necessary to deform the walls of a chamber.

The container 100 may comprise a single sealed flexible bag having multiple chambers. Alternately, the container 100 may comprise plural separate flexible bags whose necks are joined together. If the container 100 comprises separate flexible bags, the closure device between adjacent chambers may also act as a device for joining together the necks of separate bags. When the container comprises separate bags, each bag may comprise a single or multiple chambers.

The flexible container 100 must have chamber walls that are sufficiently flexible that application of pressure to the chamber walls will cause the chamber to partially collapse. The chambers may be formed from two flat sheets of flexible material that are joined along their outer edges, similar to existing blood bags. Alternately, the container walls may comprise one or more flexible sheets of material that are formed into a cylindrical shape. In yet another embodiment, the walls of the container may be formed of an elastic material that can expand and contract. In any event, the container 100 should be constructed such that the interior volume of each chamber can be reduced without wrinkling of the chamber walls, because wrinkling could trap a portion of the fluid contents of a chamber.

In addition, the container 100 must be strong enough to withstand the forces generated during centrifuging operations. The centrifuging force necessary to separate red blood cells from whole blood can exert a pressure of 100 lb/in$^2$, or more, on the walls of the container. If a holder device is provided to support the exterior walls of the container during rotation, the walls can be weaker than if the rotating device simply rotates the container without support.

The closure devices 112, 122 and 132 between the chambers 110, 120, 130 and 140 are designed to releasably seal the necks 115, 125 and 135 to prevent the contents of one chamber from flowing into an adjacent chamber. The closure devices may comprise manually or automatically controlled valves or clamps. Alternately, if the container 100 is held in a supporting device that is rotated with the container, the closure devices may comprise cams, levers, or bars that bear against an exterior wall of a neck to close off the neck.

The sensors 150, 160, 170 may comprise any type of sensor capable of sensing the flow of material through the necks 115, 125 and 135 of the container 100. For instance, a sensor may comprise a light emitting and light sensitive diode pair arranged on opposite sides of a neck. Alternately, a sensor could comprise an ultrasonic transducer that senses material passing through a neck.

If a sensor comprises a light emitting and light sensitive diode pair, the light emitting diode would emit a beam of light that passes through the neck and is received by the light sensitive diode. While a first type of fluid is moving through the neck, the amount of light received by the light sensitive diode would remain relatively constant. A sensed change in the amount of light transmitted through the neck would indicate that a different type of fluid has entered the neck.

Figure 8:
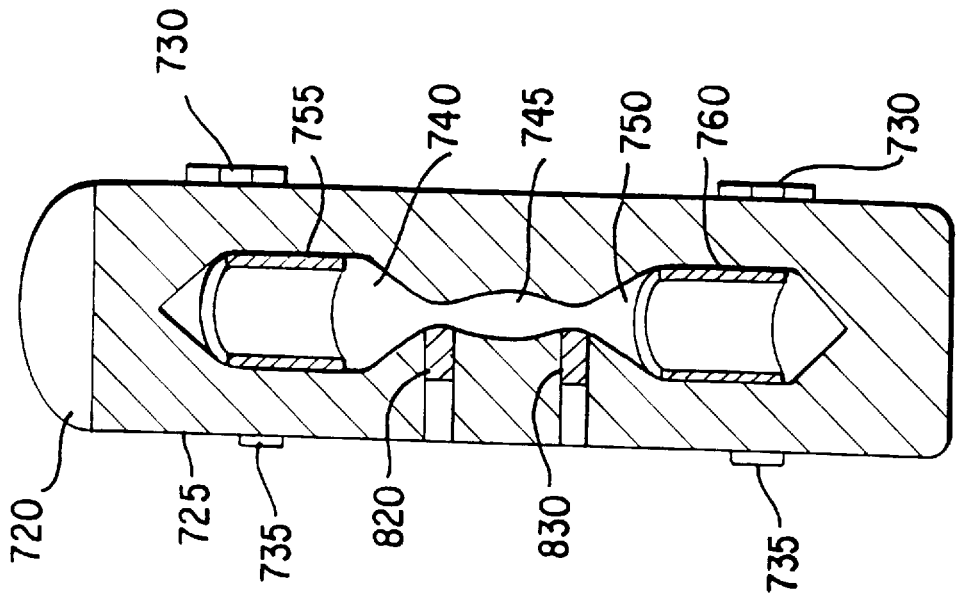
FIG. 8 is a perspective, sectional view of a device for supporting a multi-chambered, elongated, collapsible container.

A sectional view of a holder 720 embodying the invention is shown in FIG. 8. The holder is designed to support a container embodying the invention while the container is rotated. The apparatus may be used in any orientation in addition to vertical because gravity will have only a negligible effect on the contents of the container as compared to the forces of centrifugation.

The supporting device 720 may be formed from two hinged semi-cylindrical sections 725 that may be closed around a container embodying the invention. Hinges 730 may be provided along first edges of the sections 725, and closure devices 735 may be provided on opposite edges. Each section 725 of the holder may have multiple apertures 740, 745 and 750 that surround a container mounted in the holder 720. Closure devices 820, 830 may comprise levers or bars that bear against the necks of a container mounted in the holder 720 to close of the necks. The closure devices may be spring loaded and operate based on the centrifugal forces generated when the holder is rotated. Alternately, the closure devices 820, 830 may be operated by electrically controlled solenoids or other actuating mechanisms as is known in the art.

The holder 720 may also incorporate presses 755, 760 configured to apply pressure to the exterior of a chamber of a container mounted in the holder. The presses 755, 760 may be pressure plates that operated based on the centrifugal forces generated when the holder 720 is rotated. Alternately, the presses may be operated by electrically controlled solenoids, or by compressed air or a hydraulic fluid, as is known in the art. In one embodiment of the holder the presses 755, 760 may comprise inflatable collars that are expanded by the introduction of compressed air.

Figure 9:
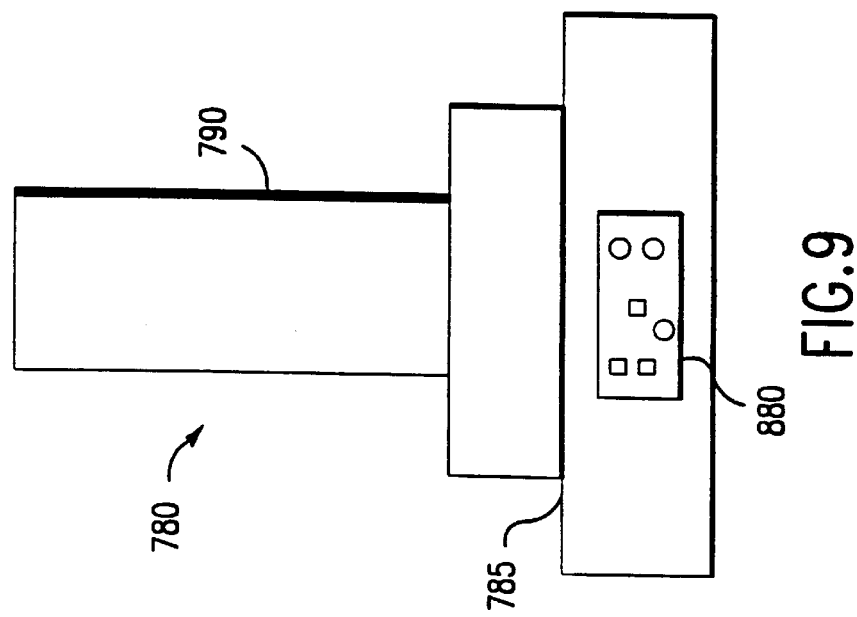
FIG. 9 is a diagram of an apparatus for holding and rotating the device shown in FIG. 8 to automatically separate a fluid and/or to automatically wash or deglycerolize a separated component of a fluid.

A centrifuge for rotating the holder 720 and a container 100 embodying the invention is shown in FIG. 9. The centrifuge 780 comprises a rotating column 790 mounted on a base 785. The centrifuge 780 includes motive means such as an electric motor for rotating the column 790. A holder 720, as shown in FIG. 8, is mounted in the column 790, and rotated to perform a separation and/or a washing or deglycerolizing operation. The centrifuge 720 may include a user interface 880 that allows the user to input specific instructions, or to select different types of operations.

Figure 10:
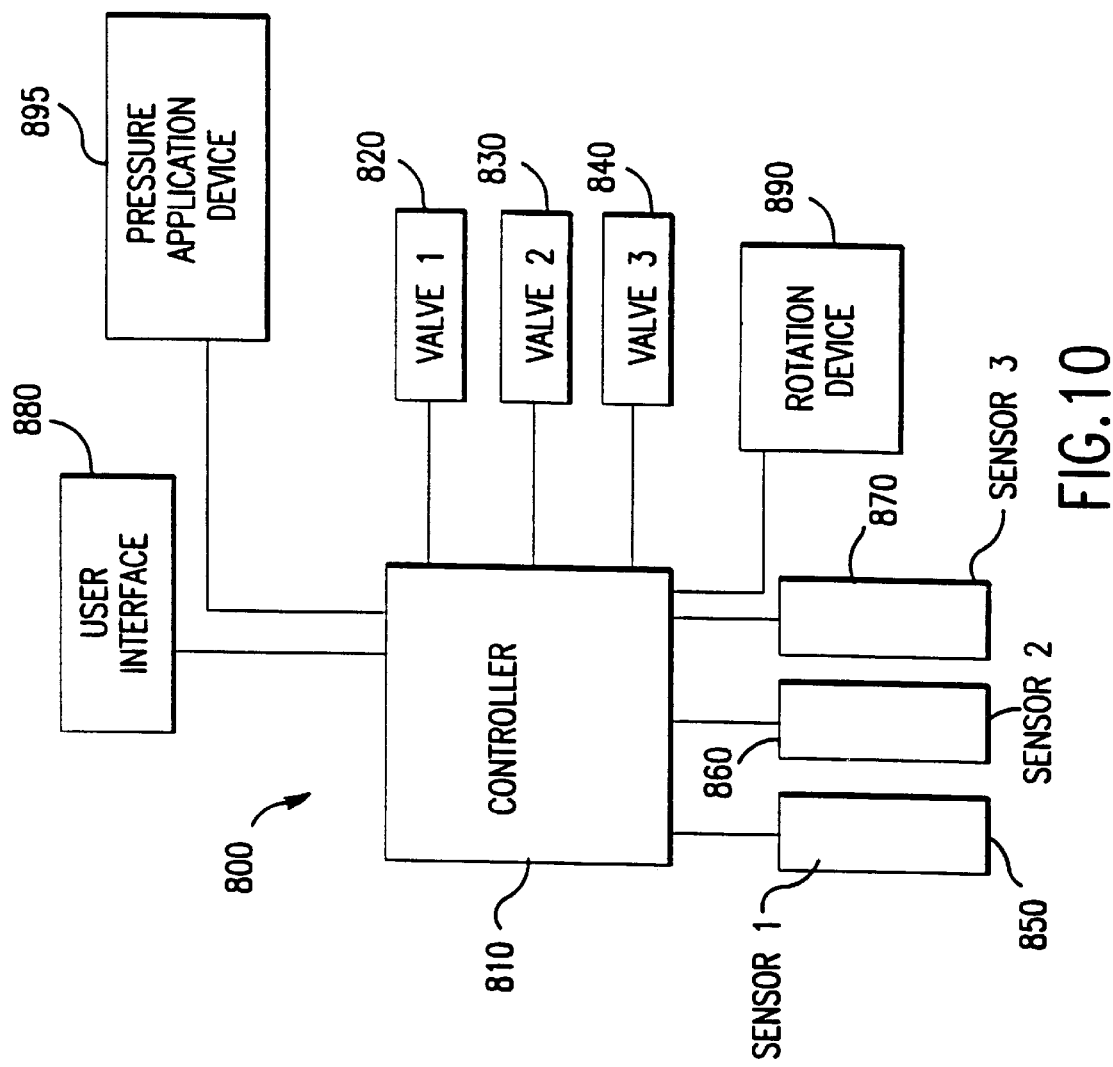
FIG. 10 is a diagram of a control system for controlling the apparatus shown in FIG. 9.

A control system capable of automatically controlling the centrifuge 780 shown in FIG. 9, and the holder 720 shown in FIG. 8, is shown in FIG. 10. The control system 800 includes a controller 810, which may comprise any type of electronic circuit or CPU. The controller 810 may be connected to sensors 850, 860 and 870 that sense the flow of material through the necks of a container embodying the invention. The controller 810 is also connected to valves 820, 830 and 840 which control the flow of material between the chambers of a container embodying the invention. A user interface 880 may be connected to the controller 810 so that a user may directly input instructions to the controller. The controller 810 is also connected to a rotation device 890 for rotating a container embodying the invention, and a pressure application device 895 that can apply pressure to individual chambers of a container embodying the invention to move material between the chambers of the container.

The control system is designed to control the rotation device 890, the valves 820, 830 and 840, and the pressure application device 895 to perform a separation and/or a washing or deglycerolization operation on a fluid or material in a container mounted in the holder. The controller of the system may be entirely controlled by a user through the user interface. Alternately, the controller may be partially or completely automated through the use of software that is stored in the controller, or on a separate storage device. Varying quantities of sensors and valves may be connected to the controller 810 depending on the exact configuration of the apparatus being controlled.

Figure 2:
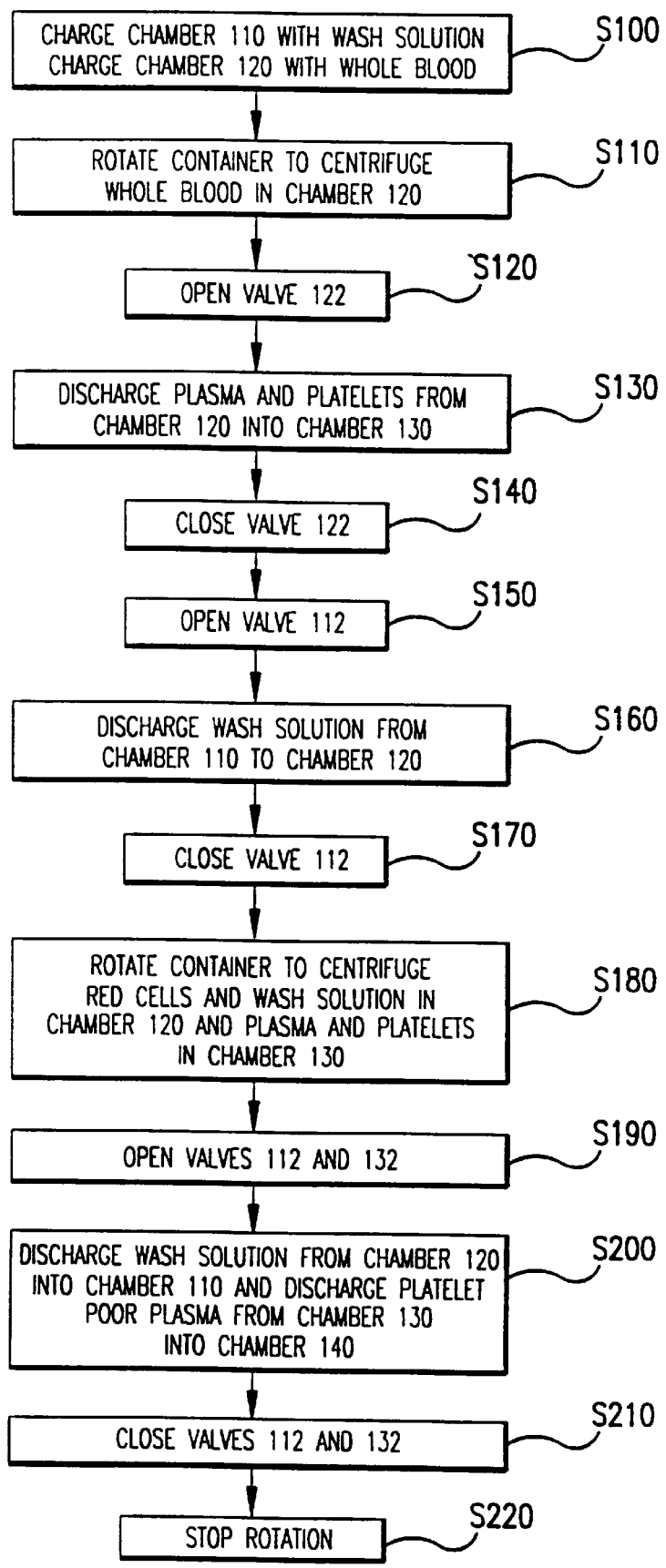
FIG. 2 is a flow chart of a method embodying the invention that utilizes the apparatus shown in FIG. 1.

A method of separating whole blood into components and of washing separated red blood cells, utilizing the apparatus of FIG. 1, will now be described with reference to the flow chart shown in FIG. 2. In the described method, the closure devices are assumed to be valves. When the method begins, each of the valves 112, 122 and 132 is closed, and both the third chamber 130 and the fourth chamber 140 are empty.

In step S100, the first chamber 110 is filled with a wash solution, and the second chamber is filled with whole blood. In step S110 the container 100 is rotated about its longitudinal axis. The rotation performs a centrifuging operation that causes red blood cells to accumulate around the outer periphery of the second chamber 120, while blood plasma and platelets collect along the longitudinal central axis of the second chamber 120.

In step S120, the valve 122 between the second chamber 120 and the third chamber 130 is opened. In step S130 blood plasma and platelets that have collected along the longitudinal central axis of the second chamber 120 are discharged into the third chamber 130 by applying pressure to the exterior of the second chamber 120. The sensor 160 adjacent the neck 125 between the second chamber 120 and the third chamber 130 senses the flow of material through the neck 125. When the sensor 160 detects that red blood cells have begun to enter the neck 125, the valve 122 is closed. These steps accomplish a separation operation that separates red blood cells in chamber 120 from blood plasma and platelets in chamber 130.

In step S150, the valve 112 between the first chamber 110 and the second chamber 120 is opened. In step S160 the wash solution in the first chamber 110 is discharged into the second chamber 120. In step S170, the valve 112 is closed. These steps cause the wash solution to mix with the red blood cells in the second chamber 120 to accomplish washing of the red blood cells. The wash solution may comprise a chloride-free, hypotonic solution at physiological pH. Alternate wash and storage solutions are described in U.S. Pat. Nos. 4,585,735 and 5,250,303 to Meryman et al., the disclosures of which are hereby incorporated by reference.

In step S180, the container 100 is rotated about the longitudinal central axis to perform a centrifuging operation on the red blood cells in the second chamber 120 and on the platelets in the third chamber 130. The centrifuging operation causes the red blood cells to collect around the periphery of the second chamber 120 and causes the platelets to collect around the outer periphery of the third chamber 130.

In step S190, the valve 112 on the neck 115 between the first chamber 110 and the second chamber 120 is opened, and the valve 132 on the neck 135 between the third chamber 130 and the fourth chamber 140 is opened. In step S200, wash solution from the center of the second chamber 120 is discharged back into the first chamber 110 by applying pressure to the exterior of the second chamber 120. At the same time, platelet poor plasma is discharged from the center of the third chamber into the fourth chamber 140 by applying pressure to the exterior of the third chamber 130.

In step S210, the valve 112 between the first chamber 110 and the second chamber 120 is closed when the sensor 150 detects that red blood cells have entered the neck 115. In addition, the valve 132 between the third chamber 130 and the fourth chamber 140 is closed when the sensor 170 detects that platelet rich plasma has entered the neck 135. In step S220, rotation of the container 100 is halted. These steps accomplish separation of the washed red blood cells in the second chamber 120 from the wash solution in the first chamber 110. These steps also accomplish separation of platelet rich plasma in the third chamber 130 from platelet poor plasma in the fourth chamber 140.

At the end of the method, the chambers may be physically separated from one another for storage or disposal. If the container comprises a single flexible bag, the chambers may be separated by clamping and cutting the necks between the chambers. If the container comprises plural separate bags, the chambers may be separated by unfastening closure devices at the necks.

The initial steps of the above-described method accomplish separation of whole blood into red blood cells, and platelet rich plasma. In the subsequent steps, washing of the separated red blood cells, and separation of the platelet rich plasma into platelets and platelet poor plasma are accomplished. The method does not require a complicated apparatus or the use of rotating seals which must be replaced after each use. In addition, the method may be accomplished by a fully automated apparatus that does not require human intervention.

Figure 3:
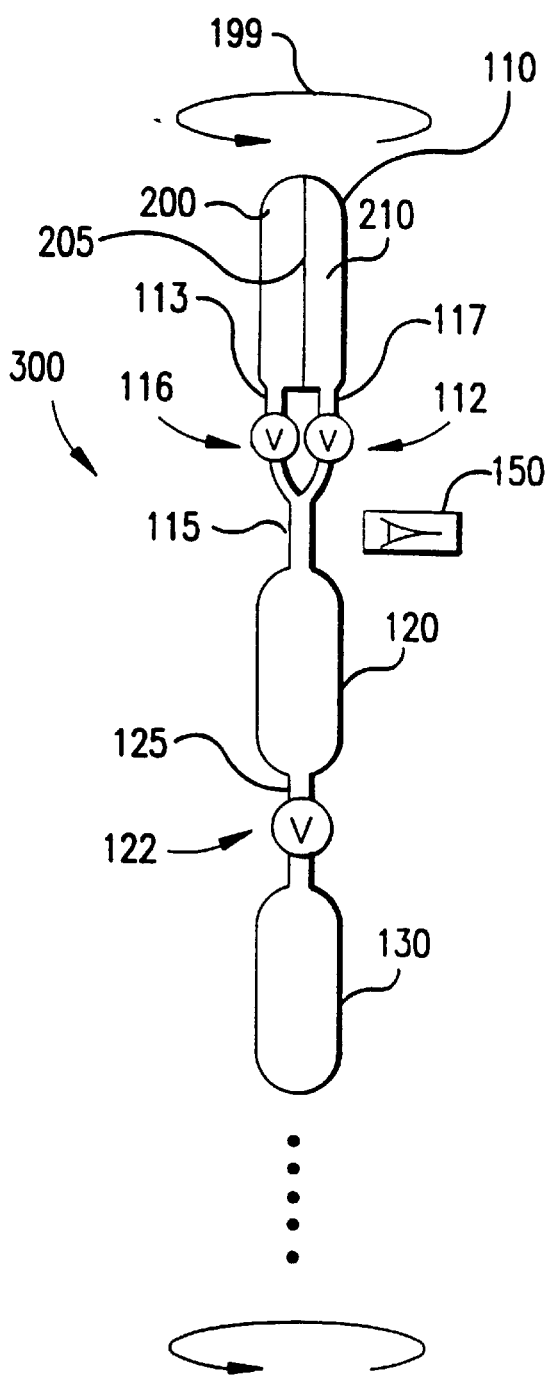
FIG. 3 is a diagram of another apparatus embodying the invention.

An apparatus embodying the invention that may be used to wash (or deglycerolize) red blood cells and to prepare the red blood cells for storage is shown in FIG. 3. The apparatus comprises a three chambered container 300 similar to the container described above. The container 300 comprises a first chamber 110 designed to contain wash solutions, a second chamber 120 designed to contain red blood cells, and a third chamber 130 designed to contain a storage solution. This type of apparatus is useful when the washed red blood cells are to be stored in a storage medium different from the wash solution.

In this apparatus, the first chamber includes a partition wall 205 that separates the first chamber 110 into two sections 200 and 210. The neck between the first chamber 110 and the second chamber 120 includes three branches. A first branch 115 leads into the second chamber 120. A second branch 113 connects the first section 200 of the first chamber 110 with the first branch 115. A third branch 117 connects the second section 210 of the first chamber 110 with the first branch 115. Closure devices 116 and 112 are installed on the second and third branches, respectively. A closure device 122 is also installed on the neck 125 between the second chamber 120 and the third chamber 130.

A sensor 150 may be mounted adjacent the first branch 115 of the neck between the first chamber 110 and the second chamber 120. The sensor 150 may be used to sense movement of material through the neck 115.

The first section 200 and the second section 210 of the first chamber 110 may be filled with two separate types of wash solutions. For instance, for deglycerolization, the first section 200 may hold a strongly hypertonic saline solution (1200 mosm) and the second section may hold a milder hypertonic saline solution (600 mosm). The first chamber 110 could include additional partition walls to further subdivide the first chamber 110 so that additional wash solutions could be used. A separate branch of the neck and a separate closure device would be provided for each such section of the first chamber 110.

The third chamber 130 may contain a red blood cell storage medium. The storage medium could be any of the storage mediums disclosed in U.S. Pat. Nos. 4,585,735 or 5,250,303 to Meryman et al., or any other commercially available storage solution such as the media sold under the tradenames Adsol, Nutricel or SAGMAN.

Figure 4:
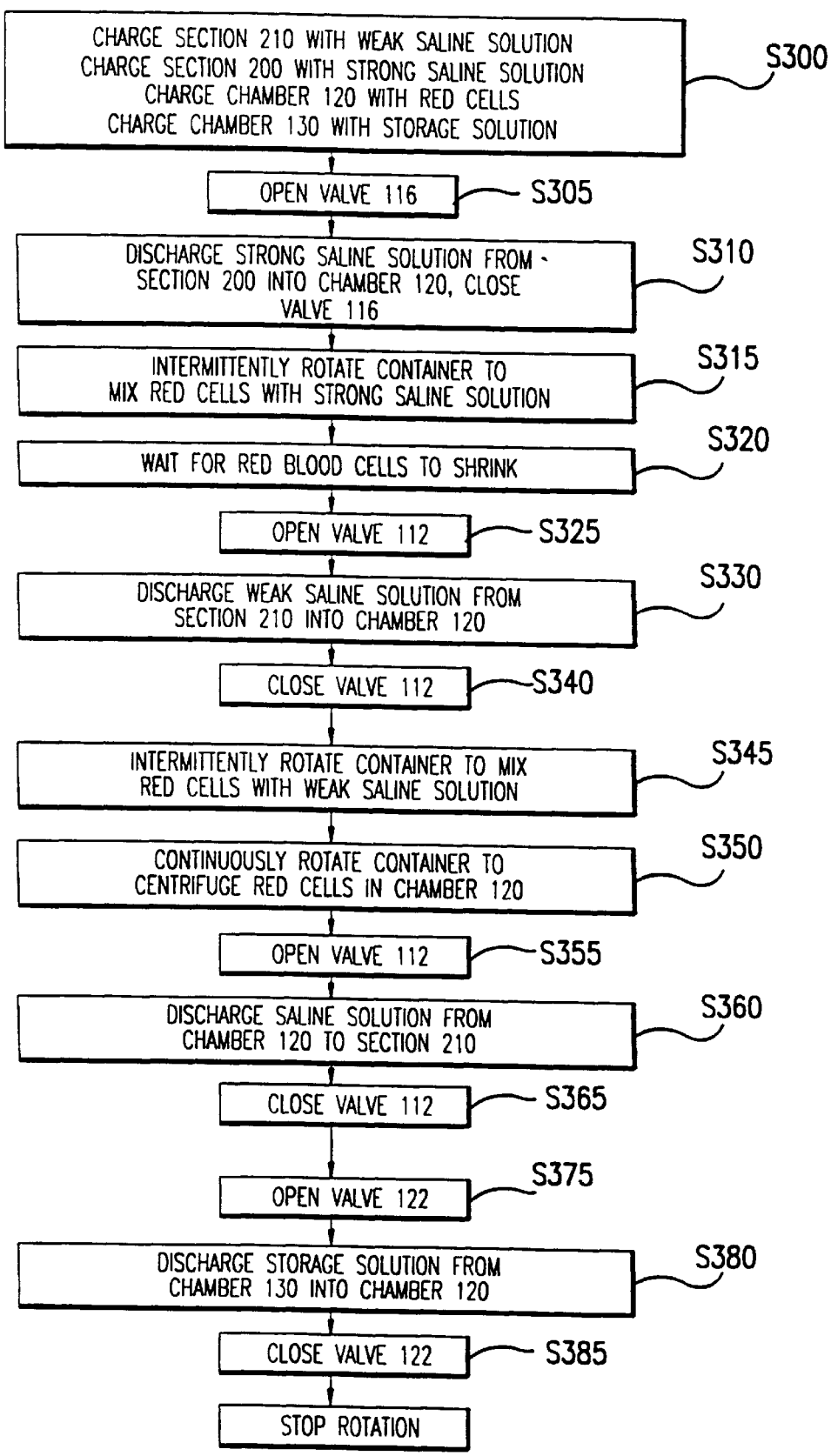
FIG. 4 is a flow chart of another method embodying the invention that utilizes the apparatus shown in FIG. 3.
Figure 5D:
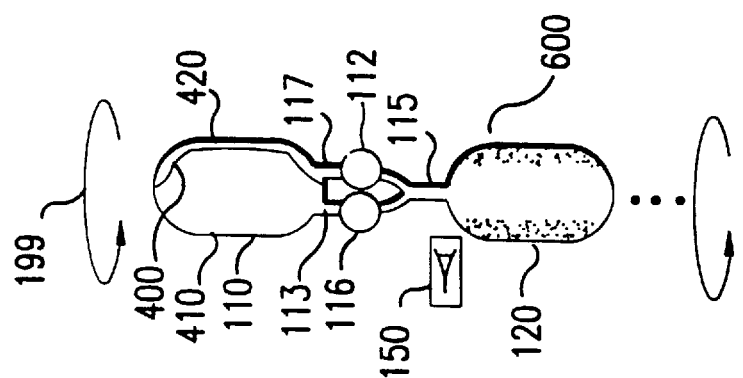
FIG. 5A–5D are diagram of another apparatus embodying the invention.
Figure 5C:
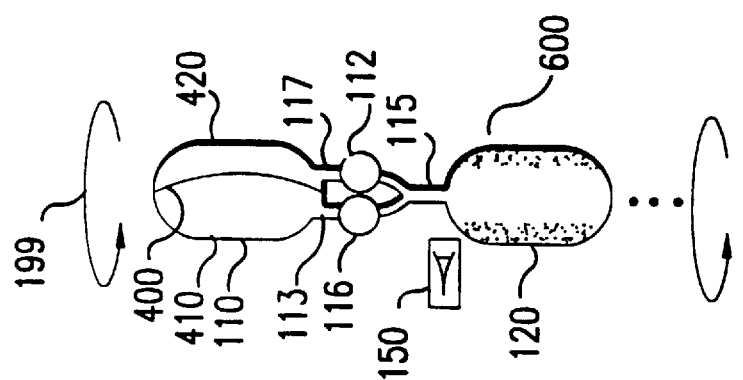
Figure 5B:
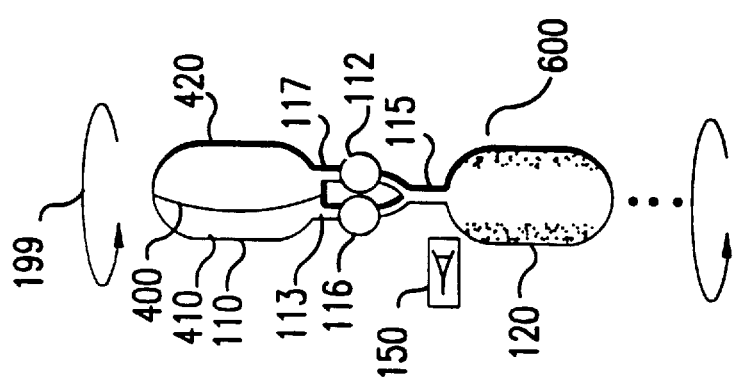
Figure 5A:
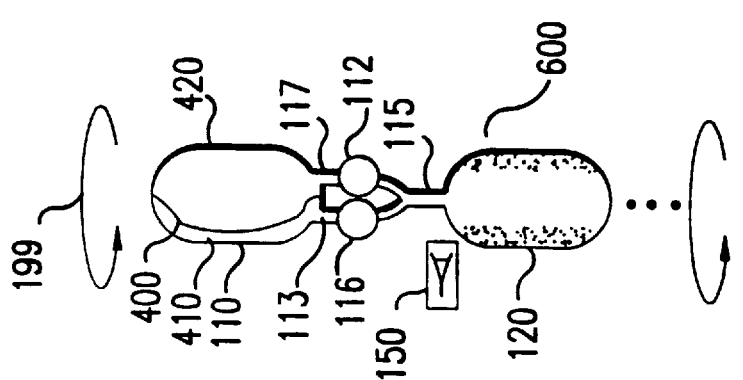

A method of deglycerolizing red blood cells in the second chamber using the apparatus shown in FIG. 3 will now be described with reference to the flowchart shown in FIG. 4. In this method it is assumed that the closure devices 112, 116 and 122 comprise valves. At the beginning of the method, each of the valves 112, 116 and 122 is closed.

In step S300, the first section 200 of the first chamber 110 is charged with a strong saline solution, the second section 210 of the first chamber 110 is charged with a weak saline solution, the second chamber 120 is charged with separated red blood cells, and the third chamber 130 is charged with a storage solution. In step S305, valve 116 is opened. In step S310, the strong saline solution is discharged from the first section 200 of the first chamber 110 into the second chamber 120, and valve 116 is closed. In step S315, the container 300, including the valves 112, 116 and 122 is intermittently rotated to thoroughly mix the red blood cells and the saline solution in the second chamber 120.

In step S320 the system pauses to allow the red blood cells to shrink after contact with the saline solution. In step S325, valve 112 is opened. In step S330 all or a portion of the weak saline solution is discharged from the second section 210 of the first chamber 110 into the second chamber 120. In step S340, valve 112 is closed. In step S345, the container 300 is intermittently rotated to thoroughly mix the saline solution and the red blood cells in the second chamber 120.

In step S350, the container 300 is continuously rotated to accomplish a centrifuging operation. This step causes the red blood cells to accumulate around the exterior of the second chamber while the saline solution collects along the longitudinal central axis of the second chamber 120.

In step S355, the valve 112 is opened. In step S360, the used saline solution is discharged from the second chamber 120 into the first section 210 of the first chamber 110. In step S365 the valve 112 is closed. These steps accomplish separation of the washed red blood cells in the second chamber 120 from the used saline solution in the first section 210 of the first chamber 110.

In each of the step wherein used wash solution is discharged from the second chamber 120 back into the first chamber, the sensor 150 may be used to determine when red blood cells enter the first branch 115 of the neck. The appropriate valve 112 or 116 can then be closed in response to the sensed presence of red blood cells in the neck.

In step S375, valve 122 between the second chamber 120 and the third chamber 130 is opened. In step S380, the storage solution in the third chamber is discharged from the third chamber into the second chamber 120. In step S385 the valve 122 is closed. These steps accomplish mixing of the washed red blood cells with a storage solution. In step S390, the rotation of the container is stopped.

In one alternative method of the above described method, the rotation of the container 300 may be halted before the storage solution has been discharged from the third chamber 130 into the second chamber 120.

In another alternative method, only a portion of the weak saline solution in the second section 210 of the first chamber 110 is discharged into the second chamber 120 in step S330. Then, after the used saline solution has been discharged from the second chamber 120 into the first section 200 of the first chamber 110, an additional portion of the weak saline solution from the second section 210 of the first chamber 110 can be used to perform an additional washing cycle.

In yet another alternative method, the red blood cells can be discharged from the second chamber 120 into the third chamber 130 after deglycerolization has been completed.

As mentioned above, the first chamber 110 may alternately comprise three or more sections, each of which contains a separate wash solution. In such an apparatus, each wash solution would be used separately to wash the red blood cells, then the used solution would be discharged back into the appropriate section of the first chamber 110.

In yet another variation of the invention, one section of the first chamber 110 may be designed to contain a wash solution, and another section of the first chamber 110 may be designed to contain a storage solution.

Another apparatus embodying the invention that may be used to wash (or deglycerolize) red blood cells and prepare the red blood cells for storage is shown in FIGS. 5A–5D. The apparatus comprises a container 600 having a first chamber 110 designed to hold a wash/storage solution, and a second chamber 120 designed to hold separated red blood cells. Closure devices 112, 116 are installed on the second branch 113 and the third branch 117 of the neck between the first chamber 110 and the second chamber 120. The second and third branches 113, 117 of the neck are connected to a first branch 115 of the neck that leads into the second chamber 120. A sensor 150 may be mounted adjacent the first branch 115 of the neck. This type of apparatus is useful when the red blood cells are to be stored in the same solution that is used for washing.

As in the apparatus described above, the container may comprise a single flexible bag having multiple chambers. Alternately, the chambers may comprise separate bags that are connected via closure devices.

In this apparatus, the first chamber 110 is separated into two sections by a partition wall 400. Prior to use, a first section 410 of the first chamber 110 will be substantially empty, and a second section 420 of the first chamber 110 will be filled with a wash/storage solution. One or more portions of the wash/storage solution in the second section 420 of the first chamber 110 can be used to wash red blood cells, and used wash/storage solution can be discharged into the first section 410 of the first chamber 110. An additional portion of the wash/storage solution can be used as a storage medium for the red blood cells.

A method of washing red blood cells and preparing them for refrigerated storage using the apparatus shown in FIGS. 5A–5D will now be described with reference to the flowchart shown in FIG. 6. In this method, it is assumed that the closure devices 112, and 116 comprise valves. At the beginning of the method, each of the valves 112, 116 is closed.

In a first step S400, the second section 420 of the first chamber 110 is charged with a wash/storage solution and the second chamber 120 is charged with separated red blood cells. At this point the apparatus will resemble the apparatus shown in FIG. 5A.

In step S405, the valve 112 between the second section 420 of the first chamber 110 and the second chamber 120 is opened. In step S410, a first portion of the wash/storage solution is discharged into the second chamber 120, where it mixes with the red blood cells. In step S415, the valve 112 is closed.

In step S420, the container 600 is rotated about the longitudinal axis, as shown by arrow 199, to accomplish a centrifuging operation. The rotation of the container 300 causes the red blood cells in the second chamber 120 to collect around the periphery of the second chamber 120, while the wash/storage solution collects along the longitudinal central axis of the second chamber 120.

In step S425, the valve 116 between the second chamber 120 and the first section 410 of the first chamber 110 is opened. In step S430, the used wash/storage solution is discharged from the second chamber 120 into the first section 410 of the first chamber 110 by applying pressure to the exterior of the second chamber 120. After these steps have been completed, the apparatus will resemble the apparatus shown in FIG. 5B.

In step S435 the valve 116 on neck leading to the first section 410 is closed, and the valve 112 on the neck leading to the second section 420 is opened. In step S440 a second portion of the wash/storage solution is discharged from the second section 420 of the first chamber 110 into the second chamber 120. In step S445 the valve 112 on the neck leading to the second section is closed. In step S455, the container 600 is continuously rotated to accomplish a centrifuging operation. The rotation of the container 600 causes the red blood cells to collect around the periphery of the second chamber 120, while the second portion of the wash/storage solution collects along the longitudinal central axis of the second chamber 120.

In step S460 the valve 116 on the neck leading to the first section 410 of the first chamber 110 is opened. In step S465 the second portion of the wash/storage solution is discharged from the second chamber 120 into the first section 410 of the first chamber 110. At this point, the apparatus will resemble the apparatus shown in FIG. 5C.

In step S470, the valve 116 leading to the first section 410 of the first chamber 110 is closed and the valve 112 leading to the second section 420 of the first chamber 110 is opened. In step S480 a last portion of the wash/storage solution is discharged from the second section 420 of the first chamber 110 into the second chamber 120. The last portion of the wash/storage solution is used as a storage medium for the washed red blood cells. In step S485 the valve 112 leading to the second section 420 of the first chamber 110 is closed. In step S490, rotation of the container is halted. At this point, the apparatus will resemble the apparatus shown in FIG. 5D.

Variations of the above described methods are also possible. For instance, the container 600 may be intermittently rotated to thoroughly mix the red blood cells with the washing solutions. In addition, the container may be rotated throughout the process, or only when wash/storage solution is discharged between chambers Moreover, the red blood cells may by subjected to more than two wash cycles prior to being stored in a storage solution.

Figure 7:
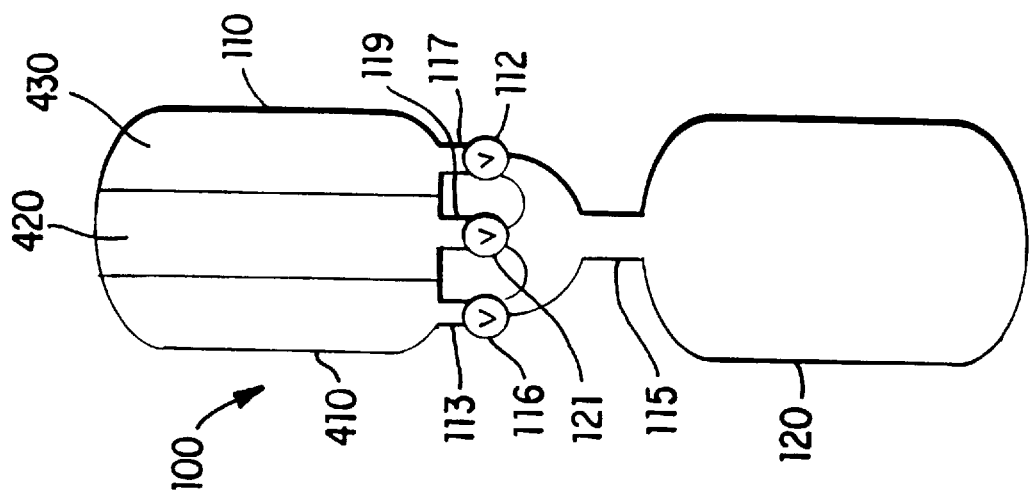
FIG. 7 is a diagram of another apparatus embodying the invention.

A red blood cell washing apparatus embodying the invention may also have a first chamber that includes three separate sections, as shown in FIG. 7. In such an apparatus 700, the first and second sections 410, 420 of the first chamber 110 could contain different wash solutions, while the third section 430 serves as a waste collection section. Alternately, the first section 410 could contain a wash solution, the second section 420 could serve as a waste solution collection section that allows the device to wash the red blood cells in plural washing operations, and the third section 430 could be filled with a storage solution that is discharged into the second chamber 120 after the red blood cells have been washed.

In addition, the method and apparatus shown in FIGS. 5A-5D, 6 and 7 may be combined with the methods and apparatus shown and described in FIGS. 1-4. For instance, the first and second chambers of the containers 600 and 700 shown in FIGS. 5A-5D and 7 may be substituted for the first and second chambers of the container 100 shown in FIG. 1. Such an apparatus would be capable of separating whole blood into components, and of washing the separated red blood cells with several cycles of wash/storage solution.

In addition, any of the above described methods may include the additional steps of intermittently rotating the container to achieve mixing, or pausing steps to wait for a chemical or physiological process to occur.

While this invention has been described in conjunction with specific embodiments thereof, it is evident that many alternatives, modifications and variations will be apparent to those skilled in the art. Accordingly, the preferred embodiments of the invention, as set forth herein, are intended to be illustrative and not limiting. Various changes may be made without departing from the spirit and scope of the invention as defined in the following claims.

What is claimed is:

1. An elongated collapsible container for holding a fluid during a centrifugation operation, comprising at least one flexible container wall that forms at least two chambers that are in fluid communication through at least one neck, wherein the at least two chambers are arranged longitudinally along the container, and wherein the at least two chambers and the at least one neck share said wall and have longitudinal central axises that coincide with a longitudinal central axis of the container.

2. The container of claim 1, wherein at least one of the at least two chambers includes at least one partition wall dividing the at least one chamber into at least two sections.

3. The container of claim 2, wherein a neck between the at least one chamber and an adjacent chamber of the container comprises at least two branches, and wherein each branch leads to a respective section of the at least one chamber.

4. The container of claim 1, wherein the at least one neck is closable to prevent contamination between the at least two chambers to which it is attached.

5. The container of claim 1, wherein the at least one neck is at least partially optically transparent.

6. The container of claim 1, wherein the at least one flexible container wall comprises at least two sheets of flexible material.

7. The container of claim 6, wherein portions of the at least two sheets of flexible material are joined to form the collapsible container.

8. The container of claim 1, wherein the at least one flexible container wall is formed of an elastic material.

9. The container of claim 1, wherein the at least one flexible container wall has sufficient strength to withstand the forces generated when the container is rotated, during a centrifuging operation, to separate whole blood within the container.

10. The container of claim 1, wherein the at least two chambers comprise first, second and third chambers, wherein the at least one neck comprises first and second necks, and wherein the first and second chambers are in fluid communication through the first neck and the second and third chambers are in fluid communication through the second neck.

11. The container of claim 10, wherein the first chamber includes at least one partition wall dividing the first chamber into at least two sections.

12. The container of claim 11, wherein the first neck comprises at least two branches, and wherein each branch leads to a respective section of the first chamber.

13. The container of claim 11, wherein at least one section of the first chamber contains a washing fluid.

* * * * *